United States Patent
Ott et al.

(10) Patent No.: US 12,421,480 B2
(45) Date of Patent: Sep. 23, 2025

(54) CORE-SHELL CAPSULES PREPARED WITH LINEAR AND CYCLIC ALIPHATIC POLYISOCYANATES

(71) Applicant: SYMRISE AG, Holzminden (DE)

(72) Inventors: Patrick Ott, Holzminden (DE); Kolja Behrens, Polle (DE); Timothy J. Evans-Lorra, Brooklyn, NY (US); John M. Teffenhart, Edison, NJ (US)

(73) Assignee: SYMRISE AG, Holzminden (DE)

( * ) Notice: Subject to any disclaimer, the term of this patent is extended or adjusted under 35 U.S.C. 154(b) by 935 days.

(21) Appl. No.: 17/049,070

(22) PCT Filed: Apr. 24, 2018

(86) PCT No.: PCT/EP2018/060492
§ 371 (c)(1),
(2) Date: Oct. 20, 2020

(87) PCT Pub. No.: WO2019/206404
PCT Pub. Date: Oct. 31, 2019

(65) Prior Publication Data
US 2021/0238510 A1 Aug. 5, 2021

(51) Int. Cl.
*C11D 17/00* (2006.01)
*A61K 8/11* (2006.01)
*A61Q 13/00* (2006.01)
*B01J 13/16* (2006.01)
*C08G 18/32* (2006.01)
*C08G 18/72* (2006.01)
*C08G 18/73* (2006.01)
*C08G 18/75* (2006.01)
*C11D 3/00* (2006.01)
*C11D 3/50* (2006.01)

(52) U.S. Cl.
CPC ............ *C11D 17/0039* (2013.01); *A61K 8/11* (2013.01); *A61Q 13/00* (2013.01); *B01J 13/16* (2013.01); *C08G 18/3225* (2013.01); *C08G 18/722* (2013.01); *C08G 18/73* (2013.01); *C08G 18/758* (2013.01); *C11D 3/001* (2013.01); *C11D 3/505* (2013.01); *A61K 2800/412* (2013.01); *A61K 2800/56* (2013.01)

(58) Field of Classification Search
None
See application file for complete search history.

(56) References Cited

U.S. PATENT DOCUMENTS

| | | |
|---|---|---|
| 2002/0064656 A1 | 5/2002 | Klug et al. |
| 2013/0089591 A1 | 4/2013 | Vautrin et al. |
| 2013/0095158 A1 | 4/2013 | Denuell et al. |
| 2014/0271752 A1* | 9/2014 | Zeng .............. A61K 8/84 424/59 |
| 2016/0166480 A1* | 6/2016 | Lei ............... A61Q 19/10 510/159 |
| 2017/0042143 A1 | 2/2017 | Burakowska-Meise et al. |
| 2017/0189283 A1* | 7/2017 | Sasaki ............ C11D 3/505 |
| 2018/0015009 A1* | 1/2018 | Soubiran .......... A61K 8/87 |
| 2018/0042825 A1* | 2/2018 | Lei ............... A01N 25/28 |
| 2018/0228702 A1 | 8/2018 | Aussant |

FOREIGN PATENT DOCUMENTS

| | | | |
|---|---|---|---|
| CN | 102958597 A | 3/2013 | |
| CN | 103140208 A | 6/2013 | |
| CN | 104039295 A | 9/2014 | |
| CN | 106457194 A | 2/2017 | |
| CN | 107072925 A | 8/2017 | |
| EP | 3295929 A1 | 3/2018 | |
| JP | 2013530979 A | 8/2013 | |
| JP | 2013537472 A | 10/2013 | |
| JP | 2017515661 A | 6/2017 | |
| JP | 2017533240 A | 11/2017 | |
| WO | 2013092958 A1 | 6/2013 | |
| WO | 2015023961 A1 | 2/2015 | |
| WO | 2016071151 A1 | 5/2016 | |
| WO | WO-2017089116 A1 * | 6/2017 | ............ A01N 25/28 |

OTHER PUBLICATIONS

Chinese Office Action issued on Mar. 24, 2022 for corresponding Chinese Application No. 201880092657.1.
International Search Report and Written Opinion issued on Jan. 14, 2019 for corresponding PCT Application No. PCT/EP2018/060492.
Japanese Office Action issued on Mar. 16, 2022 for corresponding Japanese Application No. 2020-560281.

* cited by examiner

*Primary Examiner* — Lorna M Douyon
(74) *Attorney, Agent, or Firm* — POLSINELLI PC

(57) ABSTRACT

The present invention relates to core-shell capsules prepared with linear and/or branched and cyclic aliphatic polyisocyanates. In particular, the present invention discloses a core-shell capsule, wherein the shell comprises or consists of a polymeric material which is produced or producible by reacting two components, the first component comprising or consisting of at least one linear aliphatic polyisocyanate and/or at least one branched aliphatic polyisocyanate having more than one isocyanate group, respectively, and at least one cyclic aliphatic polyisocyanate having more than one isocyanate group, the second component comprising or consisting of one or more crosslinking agent(s). Furthermore, a product comprising the present core-shell capsule, a process for producing the present core-shell capsules and the use of the present core-shell capsules is provided.

15 Claims, 6 Drawing Sheets

CORE-SHELL CAPSULES PREPARED WITH LINEAR AND CYCLIC ALIPHATIC POLYISOCYANATES

CROSS-REFERENCE TO RELATED APPLICATIONS

This application is a national stage application (under 35 U.S.C. § 371) of PCT/EP2018/060492, filed Apr. 24, 2018, which is incorporated herein by reference in its entirety.

FIELD OF THE DISCLOSURE

The present invention relates to core-shell capsules prepared with linear and/or branched and cyclic aliphatic polyisocyanates. In particular, the present invention discloses a core-shell capsule, wherein the shell comprises or consists of a polymeric material which is produced or producible by reacting two components, the first component comprising or consisting of at least one linear aliphatic polyisocyanate and/or at least one branched aliphatic polyisocyanate having more than one isocyanate group, respectively, and at least one cyclic aliphatic polyisocyanate having more than one isocyanate group, the second component comprising or consisting of one or more crosslinking agent(s). Furthermore, a product comprising the present core-shell capsule, a process for producing the present core-shell capsules and the use of the present core-shell capsules is provided.

BACKGROUND OF THE DISCLOSURE

There is generally a constant need in industry for providing new formulations comprising fragrances or fragrance mixtures. Fragrance mixtures with a plurality of different fragrance notes are used in large numbers and countless variations in perfumes, scent mixtures (perfume compositions) and perfuming for a wide variety of different fields of use, including for example cleaning agents, fabric softeners, washing powders, liquid laundry detergents, shower gels, shampoos, deodorants, body lotions etc.

Core/shell capsules are usually produced by fine dispersion of the core material in an aqueous phase. Then in a coacervation process or in-situ polymerisation the wall material is precipitated out of the aqueous phase and envelopes the oil droplets. The size of the oil droplets therefore directly determines the size the subsequent capsule cores. In such in-situ polymerisations, aminoplasts are very frequently employed as wall material. These aminoplasts are very frequently based on the condensation of melamine and formaldehyde or other amine components or aldehydes. Methods for producing such microcapsules are known in the art.

US 2011/118161 A1 discloses a core-shell microcapsule enclosing an odorous substance, wherein the shell is made of one or more polysiloxanes bearing one or more amino groups and one or more polyisocyanates. U.S. Pat. No. 6,586,107 B2 discloses microcapsules having walls obtained by reacting polyisocyanates with guanidine compounds, wherein the polyisocyanates consists of hexamethylene diisocyanate oligomers.

SUMMARY OF THE DISCLOSURE

Due to the rising consumer demand for new fragrance notes, there is a constant need in the perfume industry not only for novel fragrance mixtures but also for new formulations offering, for instance, improved release of the fragrance notes in different environments and stability of the fragrance mixtures. More particularly, the focus in the case of novel fragrance mixtures is directed primarily to their having, over and above their primary properties, namely their olfactory properties, additional positive secondary properties, for example higher stability under particular use conditions, high abundance, high radiance, good diffusivity (i.e. good spatial effect), fullness, power and/or naturalness, odour-boosting properties and/or even more preferably dermatological compatibility, good solubility, and toxicological compatibility.

In particular, interactions of the fragrances with other constituents of the formulation or premature evaporation of the lighter volatile components of a perfume occur very frequently. In general, this leads to the olfactory impression of the perfume changing or vanishing completely.

Encapsulation of such mixtures of fragrances offers the possibility of reducing or completely preventing interactions in the perfumed product or evaporation of the slightly volatile constituents. The use of microcapsules provides release the constituent(s) under precisely defined conditions. Thus, for example, in the case of microcapsules which contain fragrant substances, it is necessary that the microcapsules enclose the fragrances, which are generally sensitive to environmental conditions (e.g. oxidative compounds), so that they are stable in storage and that only at the moment of the desired fragrance development the microcapsules are broken open by mechanical stress.

There is still a need in the art for the provision of microcapsules having an improved shell structure in terms of improved stability and improved release properties for the respective applications, such as in cleaning agents, fabric softeners, washing powders, liquid laundry detergents, shower gels, shampoos, deodorants, body lotions and other cosmetic products. Another objective in the provision of microcapsules is a sufficient stability of the shell material so that on one hand the shell is stable enough during storage in application base to prevent bleeding of the odour/aroma compounds before the final use of the consumer product, and wherein on the other hand the release of the capsules' payload is not completely inhibited due to a stability of the shell material that is too high. Still another objective resides in the provision of microcapsules having improved sensory properties, including odour.

According to a first aspect, the present invention therefore concerns the provision of a core-shell capsule, wherein the shell comprises or consists of a polymeric material, and wherein the polymeric material is produced or producible by reacting component (A) with component (B), wherein component (A) comprises or consists of at least one linear aliphatic polyisocyanate and/or at least one branched aliphatic polyisocyanate having more than one isocyanate group, respectively, and at least one cyclic aliphatic polyisocyanate having more than one isocyanate group, preferably wherein the weight ratio of the total amount of said linear and/or branched aliphatic polyisocyanate(s) to the total amount of said cyclic aliphatic polyisocyanate(s) is in the range of 90:10 to 10:90, preferably 70:30 to 15:85, more preferably 60:40 to 20:80, most preferably 50:50 to 20:80, and component (B) comprises or consists of one or more crosslinking agent(s).

The present invention also provides a product, preferably a perfumed product, comprising the present core-shell capsule, a process for producing the present core-shell capsules and the use of the present core-shell capsule, or preferably the present product, to perfume textiles, hair, skin, surfaces and/or ambient air.

The present invention is based on the finding that reacting particular isocyanates provides a core-shell microcapsule having improved analytical and sensory properties. In particular, the present inventors have found that reacting a combination of at least one linear aliphatic polyisocyanate and/or at least one branched aliphatic polyisocyanate having more than one isocyanate group, respectively, and at least one cyclic aliphatic polyisocyanate having more than one isocyanate group with any suitable crosslinking agent(s) results in a shell structure exhibiting superior material properties of the shell material, so that the shell neither breaks/leaks too early, which would lead to bleeding of the encapsulated active ingredients, particularly fragrances/odorous compounds, nor breaks/leaks too late or is completely prevented due to a stability of the shell material that is too high. It has been surprisingly found that the combination of the present polyisocyanates further provides (chemical) stability to a wide variety of active ingredients, particularly fragrances, and the possibility for adjusting the release profile, including the release time, in dependence from the amount and/or time of mechanical load applied to the present core-shell capsules.

Since the present core-shell capsules provide controlled release of the active ingredients, preferably odour substances/fragrances, improved sensory properties in terms of odour development upon breaking of the shell is obtained. The present core-shell capsules according to the present invention allows not only the use of compounds which do not react with the active ingredients but also provides sufficient stability to the capsule shell for long periods of time.

Without wishing to be bound by any theory, it is presently assumed that particularly the combination with the at least one cyclic aliphatic polyisocyanate having more than one isocyanate group, in different concentrations, results in at least partial shielding of the reacted isocyanates. In other words, access of compounds, which at least partially break/decompose/perforate the polymer material, is sterically hindered.

The term "isocyanate" as used herein refers to the functional group having the formula R—N=C=O. A compound that has at least two isocyanate groups, i.e. at least 2, 3, 4, 5, 6, 7, 8, 9, 10, 11, 12, 13, 14, 15, 20, 50, 100, 250 isocyanate groups, is referred to as a polyisocyanate.

A molecule described herein by the term "aliphatic polyisocyanate" refers to any polyisocyanate that is non-aromatic (as defined below). Moreover, said molecule comprises at least two isocyanate groups, i.e. at least 2, 3, 4, 5, 6, 7, 8, 9, 10, 11, 12, 13, 14, 15, 20, 50, 100, 250 isocyanate groups, which are directly attached to a corresponding number of different C-atoms of the same aliphatic molecule. Said at least two C-atoms, i.e. at least 2, 3, 4, 5, 6, 7, 8, 9, 10, 11, 12, 13, 14, 15, 20, 50, 100, 250 C-atoms, of the same aliphatic molecule, to which the at least two isocyanate groups are directly attached, are non-aromatic, i.e. do not form part of a planar cyclic molecule with conjugated double bonds having 4n+2 π-electrons. More preferably, said at least two C-atoms, i.e. at least 2, 3, 4, 5, 6, 7, 8, 9, 10, 11, 12, 13, 14, 15, 20, 50, 100, 250 C-atoms, of the same aliphatic molecule are not sp2-hybridized. Hence, for example, a structure of the type $R_1R_2C=CR_3NCO$, wherein $R_1$, $R_2$ and/or $R_3$ exhibits at least one (additional) isocyanate group, is not encompassed. Still more preferably, the at least two C-atoms, i.e. at least 2, 3, 4, 5, 6, 7, 8, 9, 10, 11, 12, 13, 14, 15, 20, 50, 100, 250 C-atoms, of the same aliphatic molecule are sp3-hybridized, i.e. exhibit in addition to an isocyanate group three other substituents. With exception of said at least two C-atoms, i.e. at least 2, 3, 4, 5, 6, 7, 8, 9, 10, 11, 12, 13, 14, 15, 20, 50, 100, 250 C-atoms, of the same aliphatic molecule that carry the two or more isocyanate groups (as defined above), said aliphatic polyisocyanate molecule may comprise any structure, including one or more heteroatoms, such as nitrogen, oxygen, phosphorous and/or sulfur, aromatic structures and additional C-atoms which are sp, sp2 and/or sp3-hybridized.

Said aliphatic polyisocyanate molecule bearing the at least two isocyanate groups, i.e. at least 2, 3, 4, 5, 6, 7, 8, 9, 10, 11, 12, 13, 14, 15, 20, 50, 100, 250 isocyanate groups, may further be linear, branched, or cyclic (as defined above in terms of the first aspect of the invention) and may exhibit any substitutions, including for instance aliphatic substituents, aromatic substituents, heteroatoms, such as a halogen, particularly fluorine, chlorine, bromine and/or iodine, and/or other functional groups, such as alkoxy groups.

According to a preferred embodiment, none of the at least one linear and/or the at least one branched aliphatic polyisocyanate and of the at least one cyclic aliphatic polyisocyanate of component (A) comprise any aromatic structure(s) (i.e. the respective molecules do not comprise any aromatic structures at all).

According to another preferred embodiment, the at least one linear aliphatic polyisocyanate of component (A) does not comprise any aromatic structure, whereas the at least one branched aliphatic polyisocyanate (if present) and the at least one cyclic aliphatic polyisocyanate of component (A) comprise(s) an aromatic structure.

According to another preferred embodiment, the at least one branched aliphatic polyisocyanate of component (A) does not comprise any aromatic structure, whereas the at least one linear aliphatic polyisocyanate (if present) and the at least one cyclic aliphatic polyisocyanate of component (A) comprise(s) an aromatic structure.

According to another preferred embodiment, the at least one cyclic aliphatic polyisocyanate of component (A) does not comprise any aromatic structure, whereas the at least one linear and/or branched aliphatic polyisocyanate of component (A) comprise(s) an aromatic structure.

According to yet another preferred embodiment, the at least one linear aliphatic polyisocyanate and/or the at least one branched aliphatic polyisocyanate of component (A) do/does not comprise any aromatic structure, whereas the at least one cyclic aliphatic polyisocyanate of component (A) comprises an aromatic structure.

The linear aliphatic polyisocyanate molecule is preferably selected from $C_2$-$C_{20}$, preferably $C_3$-$C_{15}$, $C_4$-$C_{12}$, $C_5$-$C_{10}$, $C_6$-$C_9$, or $C_7$-$C_8$, linear alkyl. Preferably, the linear aliphatic molecule does not encompass any aromatic structure and/or any cyclic structure.

The branched aliphatic polyisocyanate molecule is preferably selected from $C_2$-$C_{20}$, preferably $C_3$-$C_{15}$, $C_4$-$C_{12}$, $C_5$-$C_{10}$, $C_6$-$C_9$, $C_7$-$C_8$, branched alkyl. Preferably, the branched aliphatic molecule does not encompass any aromatic structure and/or any cyclic structure.

The cyclic aliphatic polyisocyanate molecule comprises at least 1, i.e. 1, 2, 3, 4 or more, non-aromatic ring structure, wherein preferably the ring structure itself only consists of C-atoms and all of the C-atoms of the ring structure are sp3-hybridized. As a matter of course, the C-atoms of the ring structure may carry appropriate substituents. The at least 1 ring structures are preferably composed independently from each other of 3, 4, 5, 6, 7 or 8 membered rings.

Preferably, the cyclic aliphatic molecule comprises 2 to 20 C-atoms, such as 3 to 15, 4 to 12, 5 to 10, 6 to 9, or 7 to 8, C-atoms.

It will be readily understood that an isocyanurate, iminooxadiazinedione and/or uretdione formed of linear aliphatic polyisocyanate and/or branched aliphatic polyisocyanate is not a cyclic aliphatic polyisocyanate according to the present invention. Preferably, any isocyanurate, iminooxadiazinedione and/or uretdione structure is not a cyclic aliphatic polyisocyanate according to the present invention.

The linear, branched and cyclic aliphatic polyisocyanate may be present as monomer or polymer, respectively. A monomeric polyisocyanate is a molecule which is not interlinked to another molecule, particularly not through the one or more crosslinking agent(s). A polymeric polyisocyanate encompasses at least two monomers which are interlinked by the one or more crosslinking agent(s). It will be readily understood that the at least two monomers are not necessarily the same monomers but may be also different. A polymeric polyisocyanate preferably comprises at least 2 or more monomers, i.e. least 2, 3, 4, 5, 10, 20, 30, 40, 50, or 100 monomers interlinked with each other by the at least one crosslinking agent(s).

The linear, branched and/or cyclic aliphatic polyisocyanate(s) preferably exhibit(s) a limited size/molecular weight, respectively, permitting reactivity with the one or more crosslinking agent(s). Examples of suitable molecular weights preferably include approx. 100 g/mol to $5*10^4$ g/mol, preferably 120 g/mol to $2*10^4$ g/mol, 140 g/mol to $10^4$ g/mol, 160 g/mol to $5*10^3$ g/mol, 180 g/mol to $2*10^3$ g/mol, 200 g/mol to $10^3$ g/mol, 220 g/mol to 900 g/mol, 240 g/mol to 800 g/mol, 260 g/mol to 700 g/mol, 280 g/mol to 600 g/mol, 300 g/mol to 500 g/mol, 320 g/mol to 450 g/mol, or 340 g/mol to 400 g/mol.

Any number of different linear, branched and/or cyclic aliphatic polyisocyanates may be employed. For instance, at least one, i.e. at least 1, 2, 3, 4, 5, 6, 7, 8, 9, 10 different linear aliphatic polyisocyanates are employed. For instance, at least one, i.e. at least 1, 2, 3, 4, 5, 6, 7, 8, 9, 10 different branched aliphatic polyisocyanates are employed. For instance, at least one, i.e. at least 1, 2, 3, 4, 5, 6, 7, 8, 9, 10 different branched cyclic polyisocyanates are employed.

A "crosslinking agent" of compound (B) refers to any compound having at least two functional groups capable of reacting with an isocyanate under formation of a stable bond. The crosslinking agent preferably comprises at least 2, 3, 4, 5, 6, 7, 8, 9 or 10 functional groups capable of reacting with an isocyanate under formation of a stable bond.

It will be appreciated that it is not necessarily required that such a crosslinking agent is added to component (A). Rather any other molecule/s may be added to component (A) giving raise to the formation of the crosslinking agent. A preferred example of such a molecule is water. Water molecules may react with a portion of component (A) under formation of polyamines which in turn react with the remaining portion of component (A) under formation of the polymeric material.

According to a preferred embodiment of the present invention, component (A) does not comprise any aromatic polyisocyanate(s).

Within the framework of this text, aromatic polyisocyanates are compounds, wherein two or more isocyanate residues are directly bound to aromatic C-atoms, and derivatives thereof, wherein each of the derivatives comprises more than one isocyanate group and further comprises one or more groups selected from the group consisting of biuret, isocyanurate, uretdione, iminooxadiazinedione and trimethylol propane adduct. Said derivatives of aromatic polyisocyanates may also be obtained by reaction of said aromatic polyisocyanates with polyalcohols (e.g. glycerine), polyamines, polythiols (e.g. dimercaprol), and/or mixtures thereof.

In other words, preferably component (A) only encompasses the linear and/or branched and cyclic aliphatic polyisocyanate(s) as defined above.

More preferably, the linear and/or branched and cyclic aliphatic polyisocyanate(s) of component (A) according to the invention do not comprise any aromatic structures at all.

According to another preferred embodiment of the present invention, the linear or branched aliphatic polyisocyanate(s) is or are selected from the group consisting of pentamethylene diisocyanate (PDI, such as Stabio D-370N or D-376N by Mitsui Chemicals Inc., Japan), hexamethylene diisocyanate (HDI), ethyl ester lysine triisocyanate, lysine diisocyanate ethyl ester and derivatives thereof, preferably wherein each of the derivatives comprises more than one isocyanate group and optionally further comprises one or more groups selected from the group consisting of biuret, isocyanurate, uretdione, iminooxadiazinedione and trimethylol propane adduct, and/or wherein the cyclic aliphatic polyisocyanate(s) is or are selected from the group consisting of isophorone diisocyanate (IPDI), 1,3-bis(isocyanatomethyl)cyclohexane (H6XDI, such as Takenate 600 by Mitsui Chemicals Inc., Japan), 1,2-bis(isocyanatomethyl)cyclohexane, 1,4-bis(isocyanato-methyl)cyclohexane, methylenebis(cyclohexyl isocyanate) (H12MDI) and derivatives thereof, preferably wherein each of the derivatives comprises more than one isocyanate group and optionally further comprises one or more groups selected from the group consisting of biuret, isocyanurate, uretdione, iminooxadiazinedione and trimethylol propane adduct (such as TMP adduct of H6XDI, particularly Takenate D-120N by Mitsui Chemicals Inc., Japan).

Particularly preferred is/are aliphatic polyisocyanate(s) obtained from renewable resources, such as PDI (Stabio D-370N or D-376N by Mitsui Chemicals Inc., Japan). It has been found that such aliphatic polyisocyanates obtained from renewable resources do not impede the quality/properties of the core-shell capsules.

Preferably, derivatives of the linear, branched and/or cyclic aliphatic polyisocyanates are employed. A derivative as used herein is understood in its broadest meaning as a compound that is derived from a compound by a chemical reaction. Examples of derivatives encompass oligomers and/or adducts of the above mentioned linear or branched aliphatic polyisocyanate(s). Preferred oligomers are biurets, isocyanurates, uretdiones, iminooxadiazinediones and preferred adducts are trimethylol propane adducts. These oligomers/adducts are well known in the art and disclosed for instance in U.S. Pat. No. 4,855,490 A or U.S. Pat. No. 4,144,268 A. Preferably, the aliphatic polyisocyanate is present in a monomeric form and/or dimerised form (as isocyanate) only or in an oligomeric form.

Said derivatives of the linear, branched or cyclic polyisocyanates may also be obtained by reaction of said polyisocyanates with polyalcohols (e.g. glycerine), polyamines, polythiols (e.g. dimercaprol), and/or mixtures thereof.

The above mentioned compounds expressly encompass the different isomers, if present, alone or in combination. For instance, methylenebis(cyclohexyl isocyanate) (H12MDI) encompasses 4,4'-methylenebis(cyclohexyl isocyanate), 2,4'-methylenebis(cyclohexyl isocyanate) and/or 2,2'-methylenebis(cyclohexyl isocyanate).

According to an embodiment of the present invention, the crosslinking agent(s) is or are polyamines with more than one amino group or salts thereof, preferably diamines or guanidines, preferably wherein the crosslinker(s) is or are selected from the group consisting of guanidine carbonate, guanidine hydrochloride, tris(2-aminoethyl)amine, ethylenediamine, butylenediamine, propanediamine, pentane-1,5-diamine, phenylene-diamine, and linear or branched polyethyleneimines, preferably diethylenetriamine.

Preferred amines have a molecular weight of less than 200 g/mol. Exemplary amines are hydrazine, ethylenediamine, diethylenetriamine, triethylenetetramine, tetraethylene-pentamine, aminoethylpiperazine, propylenediamine, N-methyidipropylenetriamine, bis(3-aminopropyl)amine, hexamethylenediamine, and also 2,5-diamino-2,5-dimethylhexane.

The guanidine compounds are preferably used in the form of aqueous solutions. Useful aqueous solutions of guanidine compounds comprise 1 to 20% by weight of the guanidine compound (referred to the total weight of the aqueous solution), for example.

The fraction of guanidine compound, especially guanidine carbonate, in the total amount of crosslinker is preferably 50 mol % or more.

According to an alternative embodiment, the functional groups the crosslinking agent(s) may be different, such as in alkanolamines, aminothiols or thioalkohols, such as dimercaprol. Any combinations of different crosslinking agents may be employed.

The crosslinking agent(s) may be in form of (isolated) chemical compounds added to component (A). Alternatively, said crosslinking agent(s) is obtained by reaction of the at least one linear aliphatic polyisocyanate having more than one isocyanate group, the at least one branched aliphatic polyisocyanate having more than one isocyanate group, and/or the at least one cyclic aliphatic polyisocyanate having more than one isocyanate group with any other compound, i.e. cases in which the crosslinking agent(s) is/are formed in situ. An example of such other compound is water. Addition of water to a polyisocyanate may give rise to formation of the corresponding carbamic acids and their subsequent decomposition to amines and carbon dioxide.

According to another embodiment of the present invention, the capsule is a microcapsule, preferably is a microcapsule with a diameter of 2 to 500 µm, more preferably 10 to 50 µm (whereby the diameters of the microcapsules cited herein are $D_{50}$ values as defined below).

The microcapsule may have a diameter of 2 to 500 µm, such as 3 to 450 µm, 4 to 400 µm, 5 to 350 µm, 6 to 300 µm, 7 to 250 µm, 8 to 200 µm, 9 to 150 µm, 10 to 100 µm, 10 to 90 µm, 10 to 80 µm, 10 to 70 µm, and 10 to 60 µm. More preferably the diameter of the microcapsule is 10 to 50 µm, such as 20 to 40 µm or 25 to 35 µm.

The diameter of the microcapsule is preferably determined by laser diffraction using a Malvern Mastersizer 2000 (according to the manufactures instructions). Obtained intensity values of the scattered light are calculated into a $D_{50}$ value using a mathematical model, such as and preferably by Fraunhofer diffraction/approximation. The $D_{50}$ value is the particle size at which 50 vol. % of the microcapsules are finer than the $D_{50}$ value and 50 vol. % are coarser.

The microcapsule is essentially spherical in shape. Essentially spherical has the meaning that the deviation in each spatial direction is 10% or less, such as 5%, 4%, 3% or 1% or less. More preferably, the microcapsule is spherical in shape.

According to still another embodiment of the present invention, the reaction is an interfacial reaction comprising contacting a first phase comprising or consisting of component (A) with a second phase comprising or consisting of component (B), preferably wherein (i) the polyisocyanate(s) of component (A) are water-insoluble and/or (ii) the cross-linking agent(s) of component (B) is or are water-soluble.

The first phase and/or the second phase may comprise at least one solvent, respectively. It is preferred that the component (A) is essentially dissolved in the first phase, and the component (B) is essentially dissolved in the second phase. Essentially dissolved has the meaning that at least 90 wt.-%, preferably at least 98 wt.-% or 99.9 wt.-%, of component (A) and component (B) are dissolved, respectively. More preferably, component (A) and component (B) are completely dissolved in the respective solvent(s).

Suitable solvents for component (A) are organic solvents having a lower polarity than n-propanol, such as dimethylsulfoxide. Suitable solvents for component (B) are solvents having a polarity which is equal to or higher than n-propanol, such as water or a mixture of ethanol/water. Preferred solvents for component (A) are not miscible with water and do not react with the isocyanate components, for example alkyl aromatic hydrocarbons such as diisopropylnaphthalene or substituted biphenyls, paraffins, natural oils (for example sunflower oil) and low-melting fats (such as coconut oil). Examples of organic water-immiscible and inert solvents that together with the material to be encapsulated and the polyisocyanate form part of the oil phase during the production of the microcapsules include aromatic, aliphatic, and naphthenic hydrocarbons, carboxylic esters, chlorinated paraffins, oils of animal and vegetable origin, natural fats having melting points in the range from 10° C. to 35° C., liquid fat derivatives, waxes and aromatic and aliphatic ethers having a boiling point equal to or greater than 100° C. Mixtures of a plurality of solvents can also be used.

It will be readily understood that also a single solvent, preferably a solvent for component (A), may be employed. Adding of another compound, such as water, to the solvent may give rise to the at least partial conversion of the compound(s) of component (A) to one or more crosslinking agent(s) as indicated above. In course of the reaction, the other compound is preferably completely reacted with the compound(s) of component (A). Potential by-products of this reaction, such as carbon dioxide, may be completely removed from the solvent.

Accordingly, the present core-shell capsule may be provided, wherein the polymeric material is produced or producible by reacting component (A) with component (B) and wherein the polyamines of component (B) is/are obtained by a reaction of the polyisocyanates of component (A) with water, if present, i.e. the first phase comprises both components (A) and (B) and the second phase may or may not comprise any (additional, the same or different) component (B).

For cosmetic applications or the encapsulation of odorous substances, preference is given in particular to those solvents which are used broadly in the perfume industry (except for alcohols which react with the isocyanates). Examples of solvents preferred for this purpose include phthalates (such as diethyl phthalate), isopropyl myristate, benzyl benzoate, ethyl citrate, limonene or other terpenes and isoparaffins.

According to an embodiment of the present invention, the first phase is dispersed in the second phase before the interfacial reaction and wherein the first phase further comprises one or more further ingredients of the core, preferably wherein the further ingredient(s) is or are inert with respect to component (A).

The dispersion of the first phase in the second phase may be obtained by mixing the two phases, preferably through mixing by e.g. a conventional KPG stirrer. One or more further ingredients of the core may be present including compound(s) different from component (B) but which react (s) with compound (A) and/or compound(s) which is or are inert with respect to component (A).

Examples of compound(s) different from component (B) but which react(s) with compound (A) encompass monoalcohols, such as n-propanol, monoamines and/or monothiols. Said compound may be employed to modulate the reaction of components (A) and (B) in terms of adjusting a desired degree of polymerisation.

Microcapsules according to the invention may be produced using an aqueous phase containing emulsifiers, stabilizers, and/or anticoalescers. Emulsifiers may also be present in the oil phase. The amount of such additives can be, for example, in the range 0.5-10% by weight, based on the respective phase.

According to another embodiment of the present invention, the second phase further comprises one or more colloidal stabilizer(s) to prevent coalescing of the first phase, preferably wherein the stabilizer(s) is or are selected from the group consisting of cellulose derivatives, preferably carboxymethyl celluloses or salts thereof, low molecular surfactants, polyethylene oxides, and polyvinyl alcohols, polycations, preferably cationic polyvinyl alcohols, and polyanions, preferably polystyrene sulfonates, polyacrylamidosulfonates and derivatives thereof.

Polyvinyl alcohols are advantageous since they assist during preparing, storage and use of the present core-shell capsules as protective colloid.

A particularly preferred stabilizer is a polyvinyl alcohol having a quaternary ammonium salt on a side chain thereof, such as GOHSENX K-434, The Nippon Synthetic Chemical Industry, CO., LTD., Japan. Such a polyvinyl alcohol having a quaternary ammonium salt on a side chain thereof, particularly GOHSENX K-434 (The Nippon Synthetic Chemical Industry, CO., LTD., Japan), is preferably employed for core-shell capsules according to the invention used in fabric softener and assists in improved sensory performance of the core-shell capsules according to the invention giving rise to further improved sensory properties, such as odour.

According to still another embodiment of the present invention, component (B) comprises 0.5 to 4 moles, preferably 0.8 to 2 moles, of amino groups per 1 mol of isocyanate groups present in component (A).

According to an embodiment of the present invention, the core comprises one or more further ingredients selected from the group consisting of odorous substances, aroma molecules, cooling agents, TRPV1/TRPV3 modulators, dyes, dye precursors, phase change materials, catalysts for chemical reactions, adhesives, reactive substances for adhesive applications, pharmaceutical active substances, UV-filters, cosmetic active substances, plant protection active substances, insect repellents (e.g. N,N-diethyl-m-toluamid (DEET), 1,2-pentandiol or ethyl butylacetylaminopropionate), water repellents, flame retardants, agrochemicals, lubricants and solvents.

Conceivable further ingredients generally include all compounds for which there exist applications from the field of microencapsulation. Such ingredients are well known in the art. Examples include, for instance, dyes colour or dye precursors for the production of carbonless copy papers, and medicines for pharmaceutical applications. Active substances for cosmetic applications are preferred. Also preferred are active substances which are odorous substances or odorous substance compositions, in particular for application in and/or perfuming of consumer goods. Either an individual odorous substance or a mixture of odorous substances (perfume composition, odorous substance composition) can be selected. The odorous substances can be compounds both of synthetic and of natural origin.

Preferred is a core-shell capsule according to the invention, wherein the core contains one or more odorous substances/fragrances as active agent(s) selected from the group consisting of extracts of natural raw materials such as essential oils, concretes, absolutes, resins, resinoids, balsams, tinctures such as for example ambergris tincture; amyris oil; angelica seed oil; angelica root oil; aniseed oil; valerian oil; basil oil; tree moss absolute; bay oil; armoise oil; benzoin resin; bergamot oil; beeswax absolute; birch tar oil; bitter almond oil; savory oil; buchu leaf oil; cabreuva oil; cade oil; calamus oil; camphor oil; cananga oil; cardamom oil; cascarilla oil; cassia oil; cassie absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill weed oil; dill seed oil; eau de brouts absolute; oak moss absolute; elemi oil; tarragon oil; eucalyptus citriodora oil; eucalyptus oil; fennel oil; fir needle oil; galbanum oil; galbanum resin; geranium oil; grapefruit oil; guaiac wood oil; gurjun balsam; gurjun balsam oil; helichrysum absolute; helichrysum oil; ginger oil; iris root absolute; iris root oil; jasmine absolute; calamus oil; blue chamomile oil; Roman chamomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemon-grass oil; lovage oil; lime oil distilled; lime oil expressed; linaloe oil; *Litsea cubeba* oil; laurel leaf oil; mace oil; marjoram oil; mandarin oil; massoi bark oil; mimosa absolute; ambrette seed oil; musk tincture; clary sage oil; nutmeg oil; myrrh absolute; myrrh oil; myrtle oil; clove leaf oil; clove bud oil; neroli oil; olibanum absolute; olibanum oil; opopanax oil; orange flower absolute; orange oil; origanum oil; palmarosa oil; patchouli oil; perilla oil; Pew balsam oil; parsley leaf oil; parsley seed oil; petitgrain oil; peppermint oil; pepper oil; pimento oil; pine oil; pennyroyal oil; rose absolute; rosewood oil; rose oil; rosemary oil; Dalmatian sage oil; Spanish sage oil; sandalwood oil; celery seed oil: spike-lavender oil; star anise oil; styrax oil; tagetes oil; fir needle oil; tea tree oil; turpentine oil; thyme oil; Tolu balsam; tonka bean absolute; tuberose absolute; vanilla extract; violet leaf absolute; verbena oil; vetiver oil; juniper berry oil; wine lees oil; wormwood oil; wintergreen oil; ylang-ylang oil; hyssop oil; civet absolute; cinnamon leaf oil; cinnamon bark oil, and also fractions thereof, or ingredients isolated therefrom; individual odorous substances from the group of the hydrocarbons, such as for example 3-carene; alpha-pinene; beta-pinene; alpha-terpinene; gamma-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane; aliphatic aldehydes and acetals thereof such as for example hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanal diethyl acetal; 1,1-dimethoxy-2,2,5-trimethyl-4-hexene; citronellyloxyacetaldehyde; 1-(1-methoxypropoxy)-(E/Z)-3-hexene; aliphatic ketones and oximes thereof such as for example 2-heptanone; 2-octanone; 3-octanone; 2-nonanone;

5-methyl-3-heptanone; 5-methyl-3-heptanone oxime; 2,4,4,7-tetramethyl-6-octen-3-one; 6-methyl-5-hepten-2-one; aliphatic sulfur-containing compounds such as for example 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol; aliphatic nitriles such as for example 2-nonenoic acid nitrile; 2-undecenoic acid nitrile; 2-tridecenoic acid nitrile; 3,12-tridecadienoic acid nitrile; 3,7-dimethyl-2,6-octadienoic acid nitrile; 3,7-dimethyl-6-octenoic acid nitrile; esters of aliphatic carboxylic acids such as for example (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl-2-methyl pentanoate; ethyl hexanoate; allyl hexanoate; ethyl heptanoate; allyl heptanoate; ethyl octanoate; ethyl-(E,Z)-2,4-decadienoate, in particular ethyl-2-trans-4-cis-decadienoate; methyl-2-octinate; methyl-2-noninate; allyl-2-isoamyloxyacetate; methyl-3,7-dimethyl-2,6-octadienoate; 4-methyl-2-pentyl crotonate; formates, acetates, propionates, isobutyrates, butyrates, isovalerates, pentanoates, hexanoates, crotonates, tiglinates or 3-methyl-2-butenoates of acyclic terpene alcohols such as for example citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-2,6-dimethyl-5,7-octadien-2-ol; 2,6-dimethyl-3,5-methyl-6-methylene-7-octen-2-ol; octadien-2-ol; 3,7-dimethyl-4,6-octadien-3-ol; 3,7-dimethyl-1,5,7-octatrien-3-ol; 2,6-dimethyl-2,5,7-octatrien-1-ol; acyclic terpene aldehydes and ketones such as for example geranial; neral; citronellal; 7-hydroxy-3,7-dimethyloctanal; 7-methoxy-3,7-dimethyloctanal; 2,6,10-trimethyl-9-undecenal; geranyl acetone and also dimethyl and diethyl acetals thereof; in particular the dimethyl and diethyl acetals of geranial, neral, 7-hydroxy-3,7-dimethyloctanal; formates, acetates, propionates, isobutyrates, butyrates, isovalerates, pentanoates, hexanoates, crotonates, tiglinates and 3-methyl-2-butenoates of cyclic terpene alcohols such as for example menthol; isopulegol; alpha-terpineol; terpinenol-4; menthan-8-01; borneol; menthan-7-ol; borneol; isoborneol; linalool oxide; nopol; cedrol; ambrinol; vetiverol; guaiol; cyclic terpene aldehydes and ketones such as for example menthone; isomenthone; 8-mercaptomenthan-3-one; carvone; camphor; fenchone; alpha-ionone; beta-ionone; alpha-n-methyl ionone; beta-n-methyl ionone; alpha-isomethyl ionone; beta-isomethyl ionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8 (5H)-one; 2-methyl-4-(2,6,6-trimethyl-1-cyclohexen-1-yl)-2-butenal; nootkatone; dihydronootkatone; 4,6,8-megastigmatrien-3-one, alpha-sinensal; beta-sinensal; acetylated cedar wood oil (methylcedryl ketone); cyclic and cycloaliphatic ethers such as for example cineole; cedryl methyl ether; cyclododecyl methyl ether; 1,1-dimethoxycyclododecane; (ethoxymethoxy)cyclododecane; alpha-cedrene epoxide; 3a, 6,6,9a-tetramethyldodecahydronaphtho[2,1-b]furan; 3a-ethyl-6,6,9a-trimethyldodeca-hydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane; cyclic and macrocyclic ketones such as for example 4-tert.-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert.-pentylcyclohexanone; 5-cyclohexadecen-1-one; 6,7-dihydro-1,1,2,3,3-pentamethyl-4 (5H)-indanone; 8-cyclohexadecen-1-one; 7-cyclohexadecen-1-one; (7/8)-cyclohexadecen-1-one; 9-cycloheptadecen-1-one; cyclopentadecanone; cyclohexadecanone; cycloaliphatic aldehydes such as for example 2,4-dimethyl-3-cyclohexene carbaldehyde; 2-methyl-4-(2,2,6-trimethylcyclohexen-1-yl)-2-butenal; 4-(4-hydroxy-4-methylpentyl)-3-cyclohexenecarbaldehyde; 4-(4-methyl-3-penten-1-yl)-3-cyclohexene carbaldehyde; cycloaliphatic ketones such as for example 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl-2,6,10-trimethyl-2,5,9-cyclododecatrienyl ketone; tert.-butyl-(2,4-dimethyl-3-cyclohexen-1-yl) ketone; esters of cyclic alcohols such as for example 2-tert.-butylcyclohexyl acetate; 4-tert.-butylcyclohexyl acetate; 2-tert.-pentylcyclohexyl acetate; 4-tert.-pentylcyclohexyl acetate; 3,3,5-trimethylcyclohexyl acetate; decahydro-2-naphthyl acetate; 2-cyclopentylcyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5- or 6-indenyl acetate; 4,7-methano-3a,4,5,6,7,7a-hexahydro-5- or 6-indenyl propionate; 4,7-methano-3a,4,5,6,7,7a-hexahydro-5- or 6-indenyl isobutyrate; 4,7-methanooctahydro-5- or 6-indenyl acetate; esters of cycloaliphatic alcohols such as for example 1-cyclohexylethyl crotonate; esters of cycloaliphatic carboxylic acids such as for example allyl-3-cyclohexyl propionate; allylcyclohexyl oxyacetate; cis- and trans-methyl dihydrojasmonate; cis- and trans-methyl jasmonate; methyl-2-hexyl-3-oxocyclopentane carboxylate; ethyl-2-ethyl-6,6-dimethyl-2-cyclohexene carboxylate; ethyl-2,3,6,6-tetramethyl-2-cyclohexene carboxylate; ethyl-2-methyl-1,3-dioxolane-2-acetate; esters of araliphatic alcohols and aliphatic carboxylic acids such as for example benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha, alpha-dimethylphenylethyl acetate; alpha, alpha-dimethylphenylethyl butyrate; cinnamyl acetate; 2-phenoxyethyl isobutyrate; 4-methoxybenzyl acetate; aralipatic ethers such as for example 2-phenyl ethyl methyl ether; 2-phenyl ethyl isoamyl ether: 2-phenyl ethyl-1-ethoxyethyl ether; phenyl acetaldehyde dimethyl acetal; phenyl acetaldehyde diethyl acetal; hydratropaldehyde dimethyl acetal; phenyl acetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin; aromatic and araliphatic aldehydes such as for example benzaldehyde; phenylacetaldehyde; 3-phenylpropanal; hydratropaldehyde; 4-methylbenzaldehyde; 4-methylphenylacetaldehyde; 3-(4-ethylphenyl)-2,2-dimethylpropanal; 2-methyl-3-(4-isopropylphenyl) propanal; 2-methyl-3-(4-tert.-butyl phenyl) propanal; 2-methyl-3-(4-isobutlyphenyl) propanal; 3-(4-tert.-butylphenyl) propanal; cinnamaldehyde; alpha-butylcinnamaldehyde; alpha-amylcinnamaldehyde; alpha-hexylcinnamaldehyde; 3-methyl-5- phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl) propanal; 2-methyl-3-(4-methylenedioxyphenyl) propanal; aromatic and araliphatic ketones such as for example acetophenone; 4-methylacetophenone; 4-methoxyacetophenone; 4-tert.-butyl-2,6-dimethylacetophenone; 4-phenyl-2-butanone; 4-(4-hydroxyphenyl)-2-butanone; 1-(2-naphthalenyl) ethanone; 2-benzofuranylethanone; (3-methyl-2-benzofuranyl) ethanone; benzophenone; 1,1,2,3,3,6-hexamethyl-5-indanyl methyl ketone; 6-tert.-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3,5,5,6,8,8-hexamethyl-2-acetonaphthone; aromatic and araliphatic carboxylic acids and esters thereof such as for example benzoic acid; phenylacetic acid; methyl benzoate; ethyl benzoate; hexyl benzoate; benzyl benzoate; methylphenyl acetate; ethylphenyl acetate; geranylphenyl acetate; phenylethylphenyl acetate; methyl cinnamate; ethyl cinnamate; benzyl cinnamate; phenylethyl cinnamate; cinnamyl cinnamate; allyl phenoxy acetate; methyl salicylate; isoamyl salicylate; hexyl salicylate; cyclohexyl salicylate; cis-3-hexenyl salicylate; benzyl salicylate; phenylethyl salicylate; methyl-2,4-dihydroxy-3,6-dimethylbenzoate; ethyl-3-phenyl glycidate; ethyl-3-methyl-3-phenyl glycidate; nitrogen-containing aromatic compounds such as for example 2,4,6-trinitro-1,3-dimethyl-5-tert.-butylbenzene; 3,5-dinitro-2,6-dimethyl-4-tert.-butyl acetophenone; cinnamonitrile; 3-methyl-5-phenyl-2-pentenoic acid nitrile; 3-methyl-5-phenylpentanoic acid nitrile; methyl anthranilate; methyl-N-methyl anthranilate; Schiff bases of methyl anthranilate with 7-hydroxy-3,7-dimethyloctanal, 2-methyl-3-(4-tert.-line; 6-isobutyl quinoline; 6-sec.-butyl quinoline; 2-(3-phenylpropyl)pyridine; indole; skatole; 2-methoxy-3-isopropylpyrazine; 2-isobutyl-3-methoxypyrazine; phenyl ethers and phenyl esters such as for example estragole; anethole; eugenyl methyl ether; isoeugenyl methyl ether; diphenyl ether; beta-naphthyl methyl ether; beta-naphthyl ethyl ether; beta-naphthyl isobutyl ether; 1,4-dimethoxybenzene; eugenyl acetate; p-cresyl phenyl acetate; heterocyclic compounds such as for example 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one; and lactones such as for example 1,4-octanolide; 3-methyl-1,4-octanolide; 1,4-nonanolide; 1,4-decanolide; 8-decen-1,4-olide; 1,4-undecanolide; 1,4-dodecanolide; 1,8-decanolide; 1,5-dodecanolide; 4-methyl-1,4-decanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene-1,12-dodecanedioate; ethylene-1,13-tridecanedioate; coumarin; 2,3-dihydrocoumarin; octahydrocoumarin, Further examples of odorous substances are known from literature, such as from the book "Perfume and Flavor Chemicals", edited by S. Arctander, 1969, Montclair N.J. (USA).

It is particularly preferred the core comprises one or more odorous substances selected from the group consisting of extracts of natural raw materials and also fractions thereof, or ingredients isolated therefrom; individual odorous substances from a group of hydrocarbons; aliphatic aldehydes and acetals thereof, aliphatic ketones and oximes thereof; aliphatic sulfur-containing compounds; aliphatic nitriles; esters of aliphatic carboxylic acids; formates, acetates, propionates, isobutyrates, butyrates, isovalerates, pentanoates, hexanoates, crotonates, tiglinates and 3-methyl-2-butenoates of acyclic terpene alcohols; acyclic terpene aldehydes and ketones and also dimethyl and diethyl acetals thereof, formates, acetates, propionates, isobutyrates, butyrates, isovalerates, pentanoates, hexanoates, crotonates, tiglinates and 3-methyl-2-butenoates of cyclic terpene alcohols; cyclic terpene aldehydes and ketones; cyclic and cycloaliphatic ethers; cyclic and macrocyclic ketones; cycloaliphatic aldehydes; cycloaliphatic ketones; esters of cyclic alcohols; esters of cycloaliphatic alcohols; esters of cycloaliphatic carboxylic acids; esters of araliphatic alcohols and aliphatic carboxylic acids; araliphatic ethers; aromatic and araliphatic aldehydes; aromatic and araliphatic ketones; aromatic and araliphatic carboxylic acids and esters thereof; nitrogen-containing aromatic compounds; phenyl ethers and phenyl esters; heterocyclic compounds; and lactones, wherein the shell is completely or substantially impervious to the odorous substance or substances.

Suitable fragrances and aromas for producing the capsules of the present invention are preferably to be found e.g. in "Riechstoffe [Fragrances]", in Steffen Arctander, in "Perfume and Flavor Chemicals", Self-published, Montclair, N.J. 1969; H. Surburg, J. Panten, in "Common Fragrance and Flavor Materials", 5th Edition, Wiley-VCH, Weinheim 2006.

The encapsulated flavour(s) and/or aroma(s) may be an aroma mixture of at least two flavours and/or aromas. Preferably, it is a mixture of at least three, four or more than five flavours and/or aromas. In most cases, the aroma mixtures are a mixture of many flavours and/or aromas. This has the advantage that the scent and taste profile of the capsules can be influenced. Suitable aroma molecules are well known in the art and may be derived from e.g. US 2017/190727 (A1). The aroma substance or these aroma substances preferably causes or cause a flavour impression, a flavour-modulating effect, a trigeminal effect and/or a salivatory stimulus.

Exemplary cooling agents comprise one or more of menthol and menthol derivatives (for example L-menthol, D-menthol, racemic menthol, isomenthol, neoisomenthol, neomenthol), menthyl ethers (for example (l-menthoxy)-1,2-propanediol, (1-menthoxy)-2-methyl-1,2-propanediol, l-menthyl methyl ether), menthyl esters (for example menthyl formate, menthyl acetate, menthyl isobutyrate, menthyl lactate, L-menthyl L-lactate, L-menthyl D-lactate, menthyl (2-methoxy)acetate, menthyl(2-methoxyethoxy)acetate, menthyl pyroglutamate), menthyl carbonates (for example menthyl propylene glycol carbonate, menthyl ethylene glycol carbonate, menthyl glycerol carbonate or mixtures thereof), the semiesters of menthols with a dicarboxylic acid or the derivatives thereof (for example monomenthyl succinate, monomenthyl glutarate, monomenthyl malonate, O-succinate N,N-(dimethyl)amide, menthyl O-menthyl succinamide), menthane carboxamides (for example menthane carboxylic acid N-ethylamide [WS3], N-alpha-(menthanecarbonyl)glycine ethyl ester [WS5], menthane carboxylic acid N-(4-cyanophenyl)amide, menthane carboxylic acid N-(alkoxyalkyl)amides), menthone and menthone derivatives (for example L-menthone glycerol ketal), 2,3-dimethyl-2-(2-propyl)-butanoic acid derivatives (for example 2,3-dimethyl-2-(2-propyl)-butanoic acid N-methylamide [WS23]), isopulegol or the esters thereof (1-(-)-isopulegol, l-(-)-isopulegol acetate), menthane derivatives (for example p-menthane-3,8-diol), cubebol or synthetic or natural blends containing cubebol, pyrrolidone derivatives of cycloalkyldione derivatives (for example 3-methyl-2 (1-pyrrolidinyl)-

2-cyclopenten-1-one) or tetrahydropyrimidin-2-ones (for example icilin or related compounds, as described in WO 2004/026840).

Menthol (L-menthol, D-menthol, racemic menthol, isomenthol, neoisomenthol, neomenthol), L-menthyl methyl ether, menthyl formate, menthyl acetate), menthone, isopulegol, I-(−)-isopulegol acetate) and cubebol have flavor effect. Suitable cooling agents are well known in the art and may be derived from e.g. US 2017/216802 (A1), US 2010/273887 (A1), EP 2 033 688 (A2) and EP 1 958 627 (A2).

TRPV1/TRPV3 modulators are known in the art and refer to transient receptor potential channels of the Vanilloid (TRPV) subfamily. TRPV1 mediates the pungent odour and pain/hot sensations associated with capsaicin and piperine. The TRPV3 protein belongs to a family of nonselective cation channels that function in a variety of processes, including temperature sensation and vasoregulation. The TRPV3 channel is directly activated by various natural compounds like carvacrol, thymol and eugenol. Several other monoterpenoids which cause either feeling of warmth or are skin sensitizers can also open the channel. Monoterpenoids also induce agonist-specific desensitization of TRPV3 channels in a calcium-independent manner.

Examples of dyes or colour formers include those which are commercially available in the art for producing carbonless copy papers and that are known not to react with isocyanates. Examples are compounds of the type of the triphenylmethane compounds, diphenylmethane compounds, bisindophthalide compounds, bisarylcarbazolylmethane compounds, xanthene compounds, benzoxazine compounds, thiazine compounds, and spiropyran compounds, especially those which are known for use as colour formers for producing carbonless copy papers. Mixtures of a plurality of colour formers can also be used. Some useful colour formers are described, for example, in EP-A 591, 106, EP-A 315,901, EP-A 234,394, DE-A 3,622,262, and EP-A 187,329.

Phase change materials are substances with a high heat of fusion which melt and solidify at a certain temperature and which are able to store and release large amounts of energy. These materials can also be classified as latent heat storage units. Examples for this kind of materials are stearic acid, paraffins and waxes. Another aspect of the present invention relates to a product, preferably a perfumed product, comprising a core-shell capsule according to the invention, preferably wherein the product is a consumer goods product selected from the group consisting of personal care products, home care products and laundry care products.

Examples of personal-care products include shampoos, rinses, hair conditioners, soaps, creams, body washes such as shower or bath salts, body soaps, body liquids, mousses, oils or gels, hygiene products, cosmetic preparations, body lotions, deodorants, antiperspirants, leave-on personal care applications including hair refreshers and lotions; personal cleaners or sanitizers; and fabric care products such as fabric refreshers. Rinse off products may be liquids, solids, pastes, or gels, of any physical form.

Examples of home-care products include solid or liquid detergents, all-purpose cleaners, fabric softeners and refreshers, ironing waters and detergents, softener and drier sheets, among which liquid, powder and tablet detergents, scent-boosters and fabric softeners are preferred.

The perfumed product may be also present in the form of fine fragrance products including perfumes, after-shave lotions and colognes.

Preferred laundry care products include detergent-containing preparations, such as powder and liquid detergents and fabric softeners. As detergents, products are included such as detergent compositions or cleaning products for washing dishes or for cleaning various surfaces, for example intended for the treatment of textiles or hard surfaces, such as floors, tiles, stone-floors, etc.

Another aspect of the present invention relates to a process for producing core-shell capsules, preferably core-shell capsules according to the present invention, comprising:
(i) Providing at least one linear aliphatic polyisocyanate and/or at least one branched aliphatic polyisocyanate having more than one isocyanate group, respectively, and at least one cyclic aliphatic polyisocyanate having more than one isocyanate group, one or more further ingredient(s) to be encapsulated, and optionally one or more solvent(s),
preferably wherein the weight ratio of the total amount of said linear and/or branched aliphatic polyisocyanate(s) to the total amount of said cyclic aliphatic polyisocyanate(s) is in the range of 90:10 to 10:90, preferably 70:30 to 15:85, more preferably 60:40 to 20:80, most preferably 50:50 to 20:80,
(ii) providing one or more crosslinking agent(s),
(iii) producing a solution (1) comprising the components of step (i), if applicable, wherein solution (1) is not water-soluble,
(iv) producing a dispersion of solution (1) in an aqueous solution (2) of the component(s) of step (ii), optionally wherein the aqueous solution (2) further comprises one or more colloidal stabilizer(s) as defined above,
(v) reacting the polyisocyanates of solution (1) with the crosslinking agent(s) of solution (2), and
(vi) optionally, subsequently maintaining the temperature of the reaction mixture in a range of 40 to 80° C. for 0.5 to 5 hours,
preferably wherein no aromatic polyisocyanate(s) are provided, reacted or used in any of the steps of said process.

As defined above, aromatic polyisocyanates are compounds, wherein two or more isocyanate residues are directly bound to aromatic C-atoms, and derivatives thereof, wherein each of the derivatives comprises more than one isocyanate group and further comprises one or more groups selected from the group consisting of biuret, isocyanurate, uretdione, iminooxadiazinedione and trimethylol propane adduct. Said derivatives of aromatic polyisocyanates may also be obtained by reaction of said aromatic polyisocyanates with polyalcohols (e.g. glycerine), polyamines, polythiols (e.g. dimercaprol), and/or mixtures thereof.

Preferably, none of the linear and/or branched and cyclic aliphatic polyisocyanates used in the process according to the invention comprise any aromatic structures at all.

It will be readily understood that the aliphatic polyisocyanates of step (i) either comprise a binary or tertiary mixture of aliphatic polyisocyanates. The binary mixtures include a mixture of at least one linear aliphatic polyisocyanate and at least one cyclic aliphatic polyisocyanate having more than one isocyanate group, respectively. An alternative binary mixture is a mixture of at least one branched aliphatic polyisocyanate and at least one cyclic aliphatic polyisocyanate having more than one isocyanate group, respectively. Preferably, a ternary mixture is encompassed of at least one linear aliphatic polyisocyanate, at least one branched aliphatic polyisocyanate, and at least one cyclic aliphatic polyisocyanate each having more than one isocyanate group, respectively. The solvent(s) possibly employed are indicated above.

Hence, a preferred core-shell capsule may be provided, wherein the shell comprises or consists of a polymeric material, and wherein the polymeric material is produced or producible by reacting component (A) with component (B), wherein component (A) comprises or consists of at least one linear aliphatic polyisocyanate having more than one isocyanate group and at least one cyclic aliphatic polyisocyanate having more than one isocyanate group, preferably wherein the weight ratio of the total amount of said linear aliphatic polyisocyanate(s) to the total amount of said cyclic aliphatic polyisocyanate(s) is in the range of 90:10 to 10:90, preferably 70:30 to 15:85, more preferably 60:40 to 20:80, most preferably 50:50 to 20:80, and component (B) comprises or consists of one or more crosslinking agent(s).

Hence, another preferred core-shell may be provided, wherein the shell comprises or consists of a polymeric material, and wherein the polymeric material is produced or producible by reacting component (A) with component (B), wherein component (A) comprises or consists of at least one branched aliphatic polyisocyanate having more than one isocyanate group and at least one cyclic aliphatic polyisocyanate having more than one isocyanate group, preferably wherein the weight ratio of the total amount of said branched aliphatic polyisocyanate(s) to the total amount of said cyclic aliphatic polyisocyanate(s) is in the range of 90:10 to 10:90, preferably 70:30 to 15:85, more preferably 60:40 to 20:80, most preferably 50:50 to 20:80, and component (B) comprises or consists of one or more crosslinking agent(s).

Hence, still another preferred core-shell may be provided, wherein the shell comprises or consists of a polymeric material, and wherein the polymeric material is produced or producible by reacting component (A) with component (B), wherein component (A) comprises or consists of at least one linear aliphatic polyisocyanate and at least one branched aliphatic polyisocyanate having more than one isocyanate group, respectively, and at least one cyclic aliphatic polyisocyanate having more than one isocyanate group, preferably wherein the weight ratio of the total amount of said linear and/or branched aliphatic polyisocyanate(s) to the total amount of said cyclic aliphatic polyisocyanate(s) is in the range of 90:10 to 10:90, preferably 70:30 to 15:85, more preferably 60:40 to 20:80, most preferably 50:50 to 20:80, and component (B) comprises or consists of one or more crosslinking agent(s).

As already indicated above the crosslinking agent provided in step (ii) may be any compound having at least two functional groups capable of reacting with an isocyanate under formation of a stable bond. The crosslinking agent preferably comprises at least 2, 3, 4, 5, 6, 7, 8, 9 or 10 (or more) functional groups capable of reacting with an isocyanate under formation of a stable bond. The functional groups may be the same, such as in polyols, polyamines or polythiols, such as glycerin, or different, such as in alkanolamines, aminothiols or thioalkohols, such as dimercaprol. Any combinations of different crosslinking agents may be employed. Polyamines are preferred crosslinking agents.

Alternatively, in step (ii) any other type of molecule/s is/are provided giving rise to the formation of the crosslinking agent(s). A preferred example of such a molecule is water. Water molecules may react with a portion of the aliphatic polyisocyanates under formation of polyamines which in turn react with the remaining portion of the aliphatic polyisocyanates under formation of a polymeric material forming the shell. Hence, step (ii) may be directed to "providing one or more molecules giving rise to the formation of the crosslinking agent(s), preferably wherein the one or more molecules giving rise to the formation of the crosslinking agent(s) comprises water." The person skilled in the art will adapt the process according to the invention accordingly in this case.

Step (v) of reacting the polyisocyanates of solution (1) with the crosslinking agent(s) of solution (2), may take place at any temperature, preferably at a temperature of 40 to 80° C., more preferably 50 to 75° C. or 60 to 70° C.

The optional step (vi) of subsequently maintaining the temperature of the reaction mixture in a range of 40 to 80° C. for 0.5 to 5 hours, is preferably conducted at the same temperature as step (v). Preferred time periods for maintaining the temperature of the reaction mixture in the desired range are 0.75 to 4 hours, such as 1 to 3 hours or 2 hours.

According to another preferred embodiment, the linear or branched aliphatic polyisocyanate(s) of step (i) is or are selected from the group consisting of pentamethylene diisocyanate (PDI, such as Stabio D-370N or D-376N by Mitsui Chemicals Inc., Japan), hexamethylene diisocyanate (HDI), ethyl ester lysine triisocyanate, lysine diisocyanate ethyl ester and derivatives thereof, preferably wherein each of the derivatives comprises more than one isocyanate group and optionally further comprises one or more groups selected from the group consisting of biuret, isocyanurate, uretdione, iminooxadiazinedione and trimethylol propane adduct, and/or wherein the cyclic aliphatic polyisocyanate(s) is or are selected from the group consisting of isophorone diisocyanate (IPDI), 1,3-bis(isocyanatomethyl)cyclohexane (H6XDI, such as Takenate 600 by Mitsui Chemicals Inc., Japan), 1,2-bis(isocyanatomethyl)cyclohexane, 1,4-bis(isocyanato-methyl)cyclohexane, methylenebis(cyclohexyl isocyanate) (H12MDI) and derivatives thereof, preferably wherein each of the derivatives comprises more than one isocyanate group and optionally further comprises one or more groups selected from the group consisting of biuret, isocyanurate, uretdione, iminooxadiazinedione and trimethylol propane adduct (such as TMP adduct of H6XDI, particularly Takenate D-120N by Mitsui Chemicals Inc., Japan).

The isomers and derivatives of the above mentioned compounds may be encompassed as indicated above.

Another aspect of the present invention relates to a core-shell capsule according the present invention is provided, which is produced or producible by a process as defined above.

Still another aspect of the present invention relates to the use of a core-shell capsule according to the present invention, or preferably of a product according to the invention, to perfume textiles, hair, skin, surfaces and/or ambient air.

This use of a core-shell capsule according to the present invention is preferably performed by employing the above mentioned product, preferably a perfumed product, comprising the present core-shell capsule. The product is preferably a consumer goods product selected from the group consisting of personal care products, home care products and laundry care products.

In the context of the present invention, the expression "have/contain" or "having/containing" designates an open enumeration and does not exclude other components apart from the expressly named components.

In the context of the present invention, the expression "consists of" or "consisting of" designates a closed enumeration and excludes any other components apart from the expressly named components.

In the context of the present invention, the expression "essentially consists of" or "essentially consisting of" designates a partially closed enumeration and designates preparations which apart from the named components only have such further components as do not materially alter the character of the preparation according to the invention.

When in the context of the present invention a preparation is described with the use of the expression "have" or "having", this expressly includes preparations which consist of said components or essentially consist of said components.

BRIEF DESCRIPTION OF THE DRAWINGS

These and other aspects of the invention will be apparent from and elucidated with reference to the embodiments described hereinafter.

DETAILED DESCRIPTION OF THE DISCLOSURE

Figure 1:
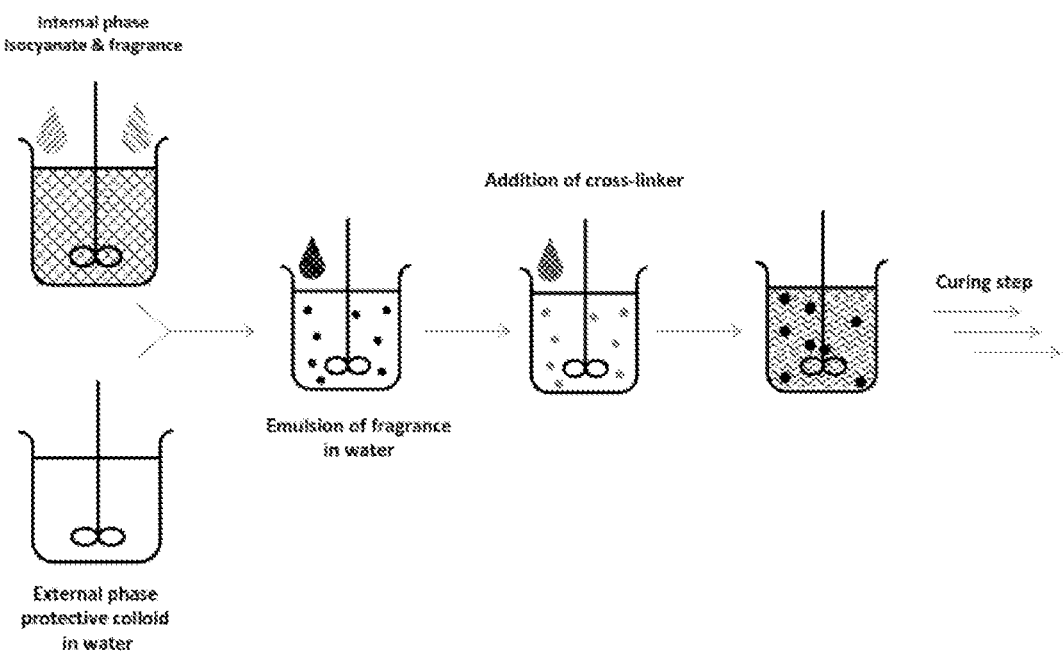
FIG. 1 shows a schematic view of a preferred embodiment of the process for producing core-shell capsules.
Figure 2:
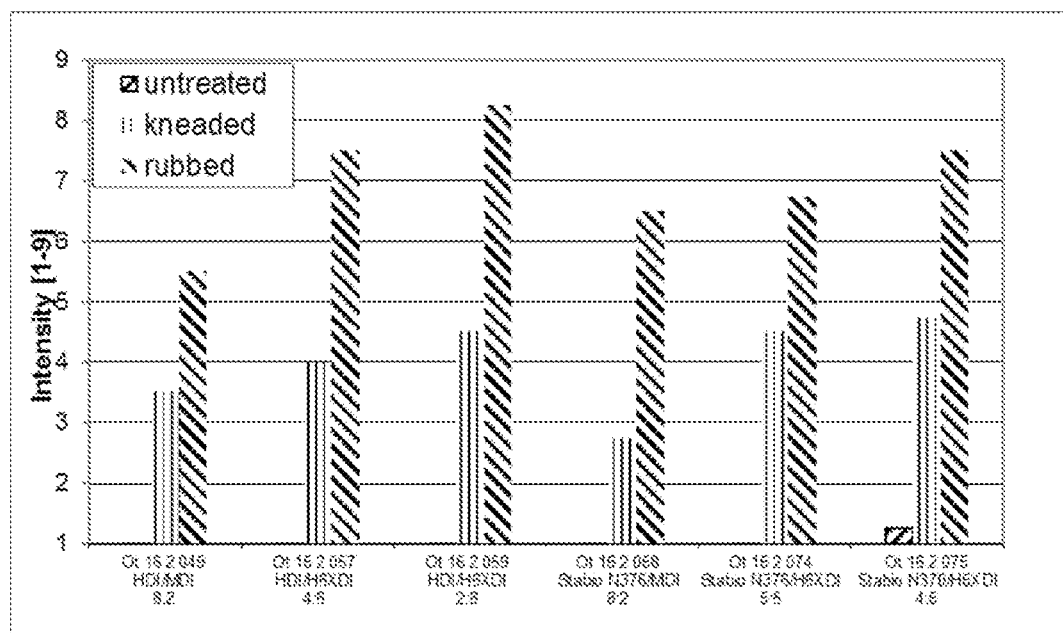
FIG. 2 shows the fragrance release from paper towels on which 0.2% aqueous dilutions of the capsule slurries have been sprayed.

In FIG. 1 a schematic view of an exemplary process according to the invention for producing core-shell capsules is shown. The internal phase is prepared by thoroughly mixing the isocyanate precursors, i.e. component (A) comprising or consisting of at least one linear aliphatic polyisocyanate and/or at least one branched aliphatic polyisocyanate having more than one isocyanate group, respectively, and at least one cyclic aliphatic polyisocyanate having more than one isocyanate group, with the fragrance and/or (an) other active ingredient(s). In a separate beaker, the external phase comprising a protective colloid is prepared in water by thoroughly mixing the constituents. In a next step the internal and external phases are thoroughly mixed for obtaining an emulsion of fragrance in water. Subsequently, the crosslinker(s) is/are added and mixing is continued until the core-shell capsules containing fragrance and/or other active ingredient(s) are cured. All steps are preferably performed under thorough mixing employing, for instance, a conventional turbine stirrer or dissolver disk. In general, high shear mixing/static mixing may be employed for preparing the emulsion.

Table 1 shows the analytical storage stabilities of the capsules in fabric softener.

TABLE 1

Examples of core-shell capsules prepared according to the invention containing the fragrance Tomcap/VOT (vegetable oil triglyceride).

|  | Ot 16 2 049 | Ot 16 2 057 | Ot 16 2 059 | Ot 16 2 068 | Ot 16 2 074 | Ot 16 2 075 |
|---|---|---|---|---|---|---|
| stability in softener test formulation fresh [%] | 94 | 93 | 98 | 97 | 95 | 96 |
| stability in softener test formulation 1 week @40° C. [%] | 81 | 81 | 89 | 86 | 84 | 87 |
| stability in softener test formulation 4 week @40° C. [%] | 73 | 73 | 86 | 76 | 81 | 76 |
| stability in softener test formulation 8 week @40° C. [%] | 70 | 67 | 84 | 70 | 73 | 68 |
| stability in softener test formulation 12 week @40° C. [%] | 66 | 62 | 82 | 63 | 63 | 54 |
| comment | capsules according to the state of the art | capsules according to the invention | capsules according to the invention | capsules according to the invention | capsules according to the invention | capsules according to the invention |
| ratio of isocyanates | see example 2 | 4:6 HDI: H6XDI | 2:8 HDI: H6XDI | see example 3 | 1:1 PDI: H6XDI | 4:6 PDI: H6XDI |
| Free oil | 0.1 | 0.0 | 0.2 | 0.1 | 0.1 | 0.1 |
| total oil | 16.8 | 13.8 | 14.1 | 16.6 | 15.3 | 16.2 |

TABLE 1-continued

Examples of core-shell capsules prepared according to the invention containing the fragrance Tomcap/VOT (vegetable oil triglyceride).

|  | Ot 16 2 049 | Ot 16 2 057 | Ot 16 2 059 | Ot 16 2 068 | Ot 16 2 074 | Ot 16 2 075 |
|---|---|---|---|---|---|---|
| particle size D50 [µm] | 22.5 | 28.7 | 25.8 | 23.2 | 25.5 | 25.8 |
| dry residue [%] | 38.7 | 34.2 | 33.8 | 34.5 | 35.5 | 33.9 |

Figure 3:
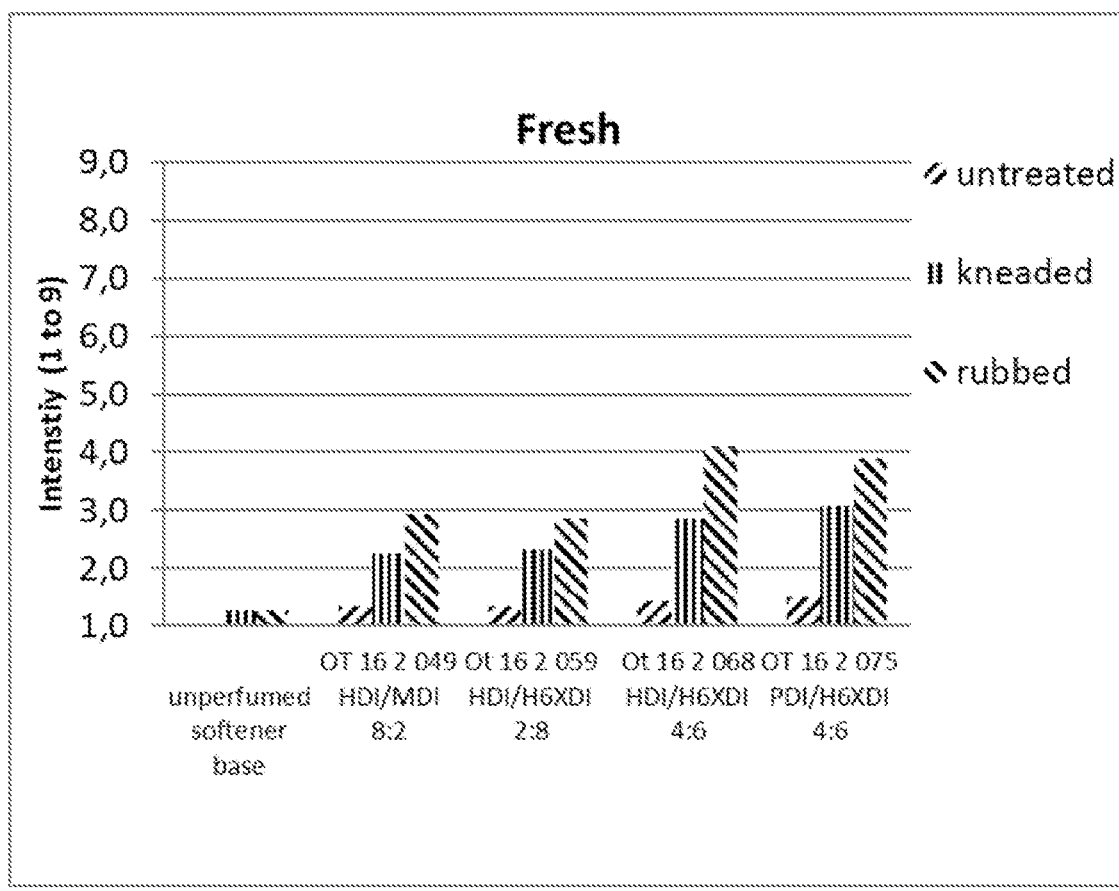
FIG. 3 shows the fragrance release of capsules from freshly prepared fabric softener samples after kneading and after rubbing of the treated test fabric.
Figure 4:
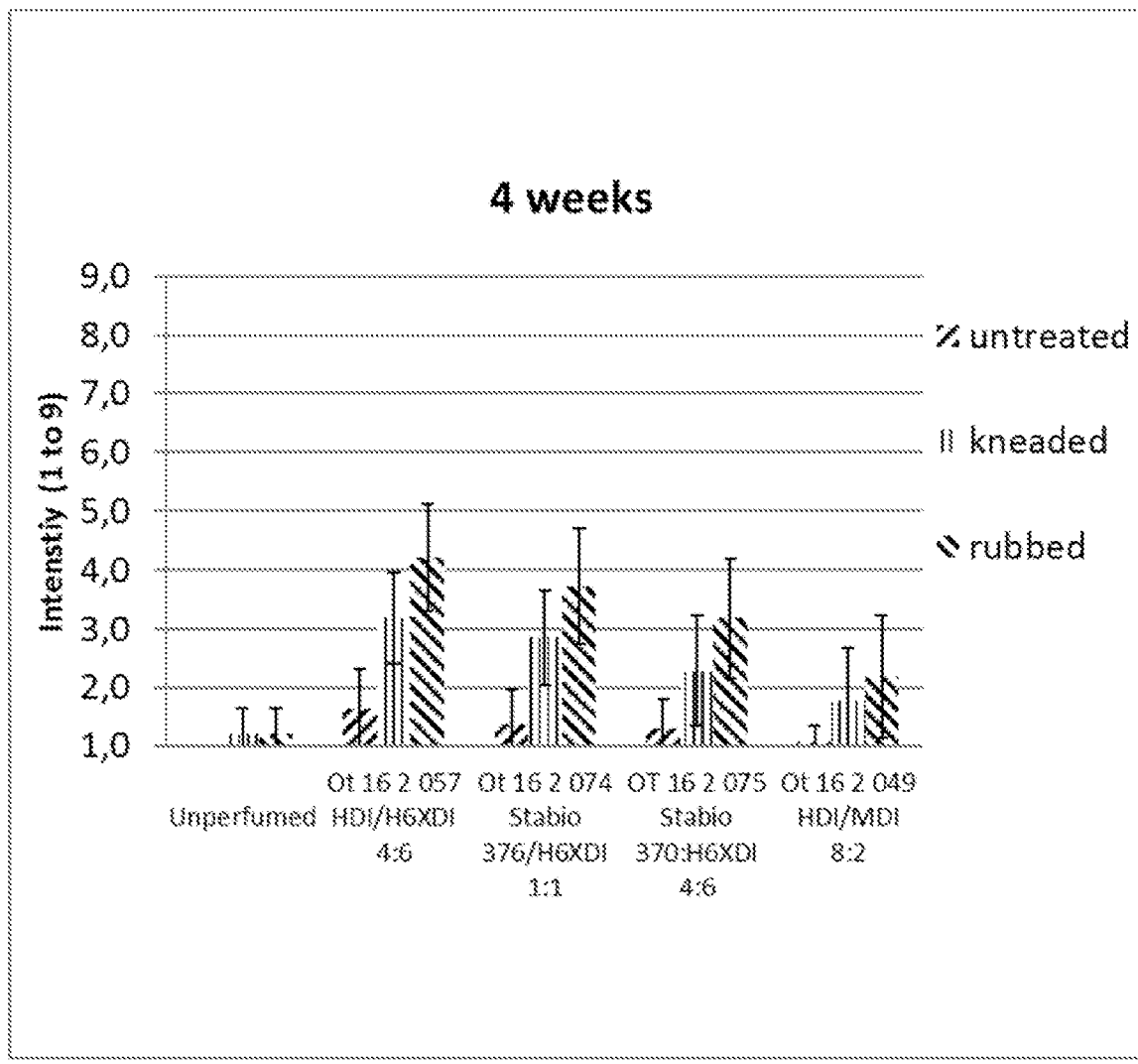
FIG. 4 shows the fragrance release from capsules stored for four weeks at 40° C. in fabric softener after kneading and after rubbing of the treated test fabric.
Figure 6:
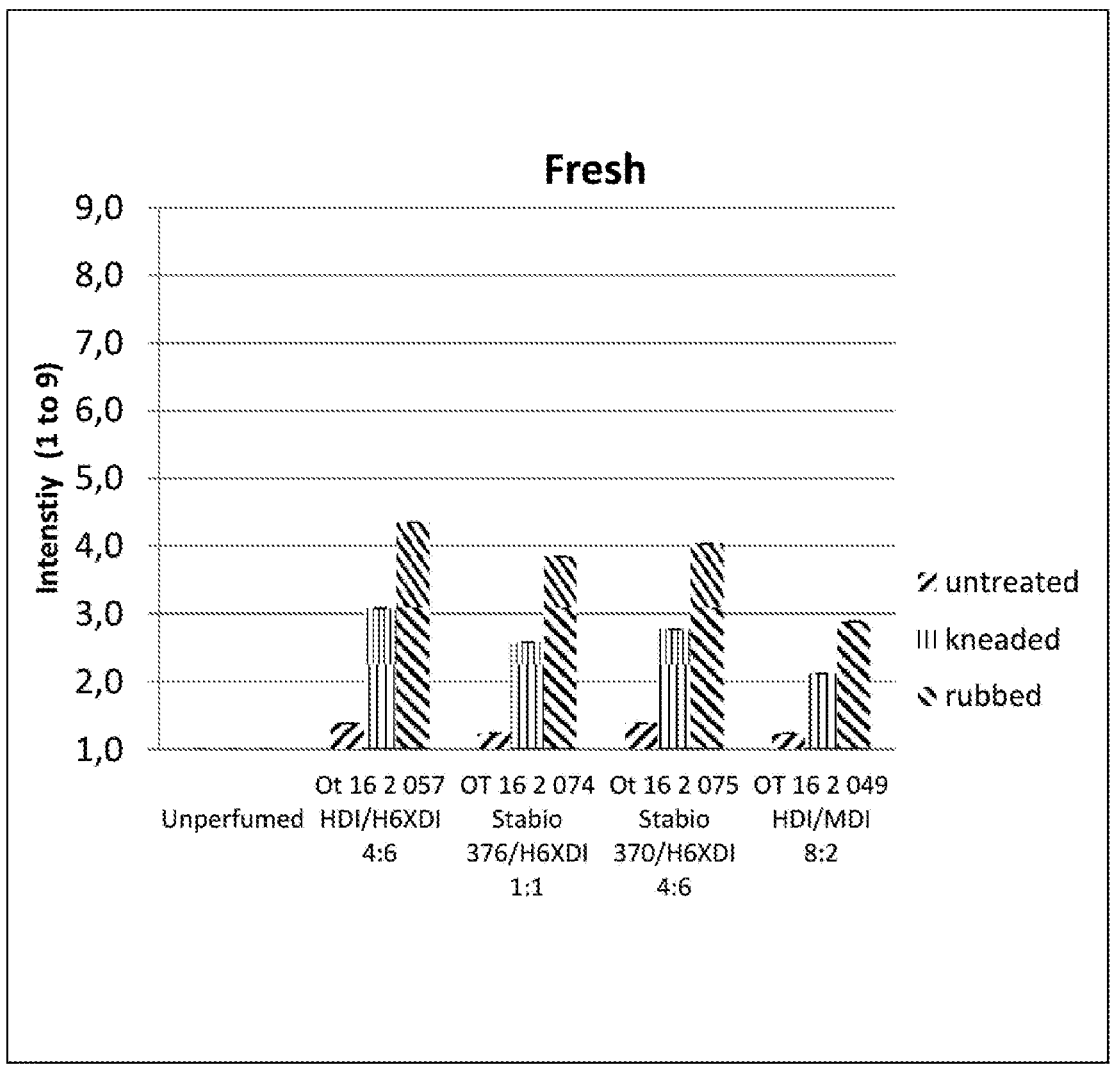
FIG. 6 shows the fragrance release of capsules from freshly prepared fabric softener samples after kneading and after rubbing of the treated test fabric.

Towels treated with fabric softener containing capsules according to the invention have been subjected to kneading and rubbing. The olfactory intensity of the samples was assessed on a scale from 1 to 9 before kneading, after kneading and after rubbing. The same has been performed for towels treated with unperfumed softener base. As expected, the unperfumed softener base does not show development of any significant odour. In all examples capsules prepared according to the invention show equal or higher intensities than the reference sample which have been prepared according to the state of the art. Capsules according to the invention freshly added to a fabric softener formulation (cf. FIG. 3) show the same tendency as capsules according to the invention after 4 weeks storage in fabric softener (cf. FIG. 4, at 40° C. and packed in plastic bags). The test shown in FIG. 3 has been repeated and the results have been confirmed (FIG. 6).

Figure 5:
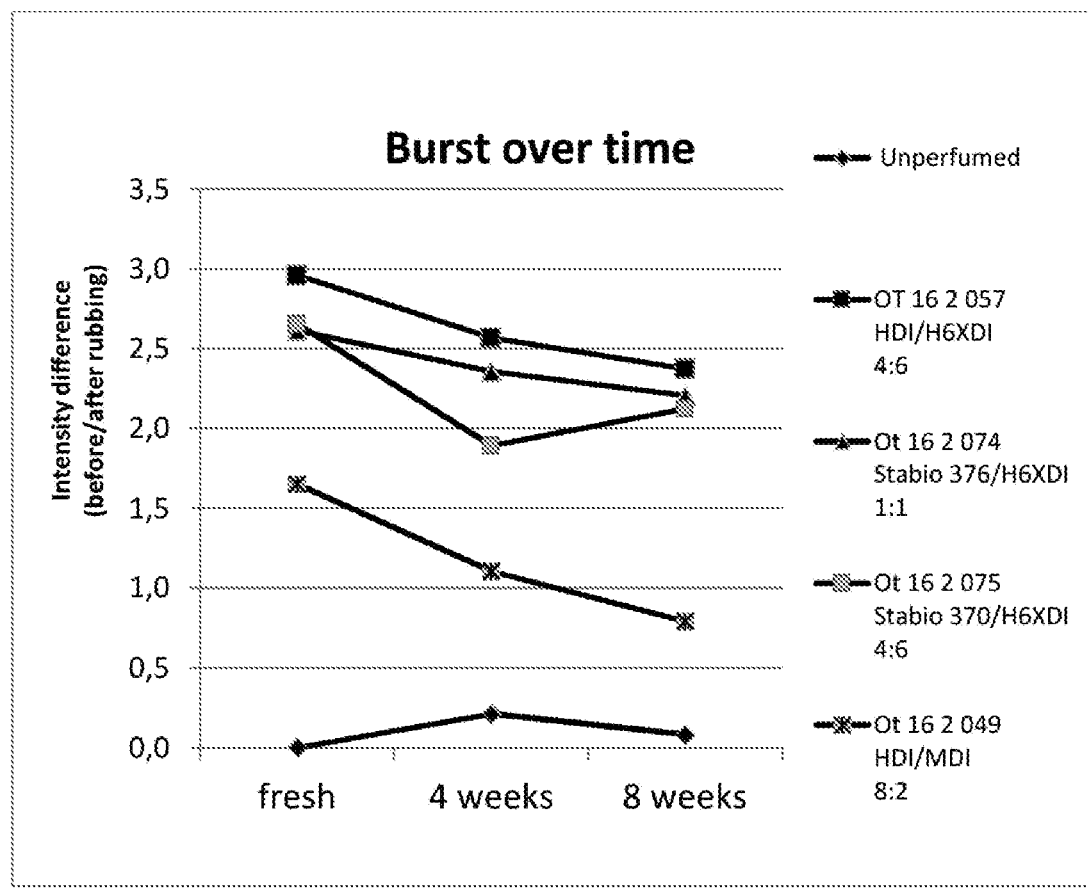
FIG. 5 shows the burst over time of core-shell capsules according to the present invention.

FIG. 5 shows the burst over storage time of the capsules in fabric softener. It is shown that all capsules prepared according to the invention show a significantly higher olfactory intensity after storage than the reference sample (capsules according to the state of the art) and unperfumed samples.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practising the claimed invention, from a study of the drawings, the disclosure, and the appended claims.

What has been stated herein with regard to the (preferred) embodiments of the core-shell capsules according to the invention applies accordingly to the products, processes and uses according to the invention described herein. Thus, the embodiments described herein are—as long as technically sensible—combinable with one another.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different independent claims does not indicate that a combination of these measures cannot be used to advantage. Any reference signs in the claims should not be construed as limiting the scope.

In the following, the present invention will be described by way of examples, wherein the present invention is not limited to the examples below.

EXAMPLES

Example 1: Capsule Slurries According to the Invention

An external phase is created by dissolving 0.7 g of polyvinylalcohol (e.g. Celvol 523, ex. Sekisui Speciality Chemicals Europe, S.L. Spain) in 250 g deionized water. 5 g of H6XDI (e.g., Takenate 600 ex. Mitsui Chemicals Inc., Japan) and 5 g of PDI (e.g. Stabio D-376N ex. Mitsui Chemicals Inc., Japan) are dissolved in 95 g 266485 TOMCAP and 95 g 192060 VEGETABLE OIL TRIGLYCERIDE (both ex. Symrise AG Holzminden). This solution is emulsified in the external phase until a particle size distribution of approx. 20 µm is reached. A solution of 5 g guanidinium carbonate in 30 g of water (ex. Aldrich, Germany) is added and the system is heated up 70° C. This temperature is kept for 2-5 h under stirring. The solution is cooled to room temperature and 0,6 g of KelcoVis DG (ex. CP Kelco, France) is added.

Example 2: Capsule Slurries According to the State of the Art

An external phase is created by dissolving 2,5 g of polyvinylalcohol (e.g. Celvol 523, ex. Sekisui Speciality Chemicals Europe, S.L. Spain) in 250 g deionized water. 2 g of MDI (Fennocap 2301, ex. Kemira Chemicals, USA) and 8 g of HDI (Desmodur N 3400, ex. Covestro, Germany) are dissolved in 95 g 266485 TOMCAP and 95 g 192060 VEGETABLE OIL TRIGLYCERIDE (both ex. Symrise AG Holzminden). This solution is emulsified in the external phase until a particle size distribution of approx. 20 µm is reached. Then a solution of 5 g guanidinium carbonate (ex. Aldrich, Germany) in 30 g of deionized water is added and the system is heated up 70° C. This temperature is kept for 2-5 h under stirring. The solution is cooled to room temperature and 0,6 g of KelcoVis DG (ex. CP Kelco, France) is added.

Example 3: Capsule Slurries According to the Invention

An external phase is created by dissolving 0.7 g of polyvinylalcohol (e.g. Celvol 523, ex. Sekisui Speciality Chemicals Europe, S.L. Spain) in 250 g deionized water. 6 g of H6XDI (e.g, Takenate 600, ex. Mitsui Chemicals Inc., Japan) and 4 g of HDI (e.g. Desmodur N 3400, ex. Covestro, Germany) are dissolved in 95 g 266485 TOMCAP and 95 g 192060 VEGETABLE OIL TRIGLYCERIDE (both ex. Symrise AG Holzminden). This solution is emulsified in the external phase until a particle size distribution of approx. 20 µm is reached. Then a solution of 5 g guanidinium carbonate in 30 g of water (ex. Aldrich, Germany) is added and the system is heated up 70° C. This temperature is kept for 2-5 h under stirring. The solution is cooled to room temperature and 0,6 g of KelcoVis DG (ex. CP Kelco, France) is added.

Example 4: Capsules not According to the Invention

An external phase is created by dissolving 0.7 g of polyvinylalcohol (e.g. Celvol 523, ex. Sekisui Speciality Chemicals Europe, S.L. Spain) in 250 g deionized water. 2 g of MDI (Desmodur M44, e.g, ex. Covestro, Germany) and 8 g of HDI (e.g. Desmodur N 3400, ex. Covestro, Germany) are dissolved 95 g 266485 TOMCAP and 95 g 192060 VEGETABLE OIL TRIGLYCERIDE (both ex. Symrise AG, Holzminden). This solution is emulsified in the external phase until a particle size distribution of approx. 20 μm is reached. Then a solution of 5 g guanidinium carbonate in 30 g of water (ex. Aldrich, Germany) is added and the system is heated up 70° C. This temperature is kept for 2-5 h under stirring. The solution is cooled to room temperature and 0,6 g of KelcoVis DG (ex. CP Kelco, France) is added.

Testing of Analytical Stability in Fabric Softeners

An unperfumed fabric softener test formulation having an ester quat content of approximately 17 wt.-% was mixed with 1 wt.-% of the capsule slurries and stored at 40° C. After a storage period of 1; 4; 8 and 12 weeks, respectively, the amount of fragrance raw materials diffused from the capsules into the base was determined with the aid of headspace measurements in the air phase above. The reported value is the percentage of fragrance oil still remaining in the capsule after storage.

Sensory Performance Testing

Method A

A 0.2% aqueous dilution of the obtained capsule dispersions are sprayed on paper towels (Katrin® Classic industrial towel XXL 2500 blue, Metsä Tissue GmbH, Kreuzau, Germany).

After drying at ambient temperature for two days the sensory performance of the samples was tested. The olfactory intensity was determined by a panel of 5 experienced testers from the towels before kneading, after kneading and after rubbing. The olfactory intensity has been judged by a scale from 1 (no scent detectable) to 9 (very strong scent).

Method B

An unperfumed fabric softener test formulation was mixed with 0.3 wt.-% of capsule slurries. These samples have been stored for 0; 1; 4 and 8 weeks, respectively. In each case 20 g of the softener capsule slurry mixture were washed onto terrycloth towels in a standard European domestic washing machine. After the spin cycle, the towels were removed from the machine and line dried. Subsequently, the olfactory intensity was determined by a panel of 11 experienced testers from the towels before kneading ("untreated"), after kneading and after rubbing. The olfactory intensity has been judged by a scale from 1 (no scent detectable) to 9 (very strong scent).

| Fabric softener test formulation | | |
|---|---|---|
| Ingredient | source | percentage by weight |
| Water, demin. | | 82.68 |
| Rewoquat WE 18 | Evonik Nutrition and Care GmbH, Germany | 16.60 |
| Parmetol K 40 | Julius Hoesch GmbH & Co. KG, Germany | 0.10 |
| Xiameter AFE-1520 | Biesterfeld Spezialchemie GmbH, Germany | 0.30 |
| Magnesium chloride | Sigma-Aldrich, Germany | 0.32 |

The invention claimed is:

1. A core-shell capsule comprising a core and a shell, the shell consisting of a product produced or producible by reacting one or more linear and/or branched aliphatic polyisocyanates having more than one isocyanate group and one or more cyclic aliphatic polyisocyanates having more than one isocyanate group with one or more crosslinking agents, wherein:
the one or more linear and/or branched aliphatic polyisocyanates are selected from the group consisting of pentamethylene diisocyanate, hexamethylene diisocyanate, ethyl ester lysine triisocyanate, lysine diisocyanate ethyl ester, and oligomers and/or adducts thereof, wherein the oligomers are biurets, isocyanurates, uretdiones, or iminooxadiazinediones and the adducts are trimethylol propane adducts, and
the one or more cyclic aliphatic polyisocyanates are selected from the group consisting of 1,3-bis(isocyanatomethyl)cyclohexane, 1,2-bis(isocyanatomethyl)-cyclohexane, 1,4-bis(isocyanatomethyl)cyclohexane, and derivatives thereof.

2. The core-shell capsule of claim 1, wherein the one or more linear and/or branched aliphatic polyisocyanates and the one or more cyclic aliphatic polyisocyanates are free of aromatic structures.

3. The core-shell capsule of claim 1, wherein the one or more crosslinking agents are selected from polyamines with more than one amino group and salts thereof.

4. The core-shell capsule of claim 3, wherein the one or more crosslinking agents contain 0.5 to 4 moles of amino groups per mole of isocyanate groups in the one or more linear and/or branched aliphatic polyisocyanates and the one or more cyclic aliphatic polyisocyanates.

5. The core-shell capsule of claim 3, wherein the one or more crosslinking agents are selected from guanidine carbonate, guanidine hydrochloride, tris(2-aminoethyl)amine, ethylenediamine, butylenediamine, propanediamine, pentane-1,5-diamine, phenylenediamine, and linear or branched polyethyleneimines, and diethylenetriamine.

6. The core-shell capsule of claim 3, wherein
the one or more linear and/or branched aliphatic polyisocyanates are selected from the group consisting of pentamethylene diisocyanate, hexamethylene diisocyanate, and oligomers and/or adducts thereof, wherein the oligomers are biurets, isocyanurates, uretdiones, or iminooxadiazinediones and the adducts are trimethylol propane adducts, and
the one or more cyclic aliphatic polyisocyanates are selected from the group consisting of 1,3-bis(isocyanatomethyl)cyclohexane, 1,2-bis(isocyanatomethyl)-cyclohexane, 1,4-bis(isocyanatomethyl)cyclohexane, and derivatives thereof.

7. The core-shell capsule of claim 6, wherein the one or more cyclic aliphatic polyisocyanates is 1,3-bis(isocyanatomethyl)cyclohexane.

8. The core-shell capsule of claim 1, wherein the capsule is a microcapsule with a diameter of 2 to 500 μm.

9. The core-shell capsule of claim 1, wherein the core comprises one or more ingredients selected from odorous substances, aroma molecules, cooling agents, transient receptor potential vanilloid 1/transient receptor potential vanilloid 3 modulators, dyes, dye precursors, phase change materials, catalysts for chemical reactions, adhesives, reactive substances for adhesive applications, pharmaceutical active substances, UV-filters, cosmetic active substances, plant protection active substances, insect repellents, water repellents, flame retardants, agrochemicals, lubricants, and solvents.

10. The core-shell capsule of claim 1, wherein the one or more linear and/or branched aliphatic polyisocyanates and the one or more cyclic aliphatic polyisocyanates are in a weight ratio of 9:1 to 1:9.

11. A product comprising the core-shell capsule of claim 1.

12. A process for producing the core-shell capsule of claim 1 comprising:
(i) providing the one or more linear and/or branched aliphatic polyisocyanates and the one or more cyclic aliphatic polyisocyanates, one or more ingredients to be encapsulated, and optionally, one or more solvents;
(ii) providing the one or more crosslinking agents;
(iii) producing a solution (I) comprising the components of (i), wherein the solution (I) is not water-soluble;
(iv) producing a dispersion of the solution (I) in an aqueous solution (II) comprising the components of (ii);
(v) reacting the one or more linear and/or branched aliphatic polyisocyanates and the one or more cyclic aliphatic polyisocyanates of the solution (I) with the one or more crosslinking agents of the solution (II); and
(vi) optionally, maintaining a reaction temperature of 40 to 80° C. for 0.5 to 5 hours.

13. A method for perfuming a textile, hair, skin, a surface, and/or ambient air comprising applying or releasing the core-shell capsule of claim 1 to the textile, the hair, the skin, the surface, and/or the ambient air.

14. A core-shell capsule comprising a core and a shell, the shell consisting of polymeric material produced or producible by reacting one or more linear and/or branched aliphatic polyisocyanates having more than one isocyanate group and one or more cyclic aliphatic polyisocyanates having more than one isocyanate group with one or more crosslinking agents, wherein:
the one or more linear and/or branched aliphatic polyisocyanates are selected from pentamethylene diisocyanate, hexamethylene diisocyanate, and oligomers and/or adducts thereof, wherein the oligomers are biurets, isocyanurates, uretdiones, or iminooxadiazinediones and the adducts are trimethylol propane adducts,
the one or more cyclic aliphatic polyisocyanates are selected from 1,3-bis(isocyanatomethyl)cyclohexane, 1,2-bis(isocyanatomethyl)-cyclohexane, 1,4-bis(isocyanatomethyl)cyclohexane, and derivatives thereof, and
the one or more crosslinking agents are selected from polyamines with more than one amino group and salts thereof.

15. The core-shell capsule of claim 14, wherein the one or more cyclic aliphatic polyisocyanates is 1,3-bis(isocyanatomethyl)cyclohexane.

* * * * *